United States Patent [19]

Sorge et al.

[11] Patent Number: 6,061,637

[45] Date of Patent: May 9, 2000

[54] METHOD OF DETERMINING KNOCK RESISTANCE RATING FOR NON-COMMERCIAL GRADE NATURAL GAS

[75] Inventors: Gregory W. Sorge, Waukesha; Richard J. Kakoczki, North Prairie; John E. Peffer, Eagle, all of Wis.

[73] Assignee: Dresser Industries, Inc., Dallas, Tex.

[21] Appl. No.: 08/932,905

[22] Filed: Sep. 17, 1997

[51] Int. Cl.$^7$ .................................................. G01L 23/22
[52] U.S. Cl. ............................... 702/24; 702/23; 702/22; 702/50; 73/35.01; 73/35.02; 73/23.31
[58] Field of Search .................................. 702/24, 23, 22, 702/27, 30, 31, 32, 50, 100, 179, 182–184, FOR 113–FOR 119, FOR 127, FOR 139, FOR 156, FOR 157, FOR 170, FOR 171; 701/111, 99, 102; 73/35.01, 35.02, 35.06, 23.31, 35.03–35.05, 1.02, 1.03; 395/300.3, 300.31, 300.33; 44/903; 123/406.16, 406.21, 406.29, 406.34, 406.37, 406.39

[56] References Cited

U.S. PATENT DOCUMENTS

| | | | |
|---|---|---|---|
| 4,010,358 | 3/1977 | Morris | 235/151.35 |
| 4,478,068 | 10/1984 | Bonitz et al. | 73/35 |
| 4,541,383 | 9/1985 | Jessel | 123/435 |
| 4,963,745 | 10/1990 | Maggard | 250/343 |

OTHER PUBLICATIONS

Callahan et al. "Engine Knock Rating of Natural Gases—Methane Number," The American Society of Mechanical Engineers, 93–ICE–18, pp. 1–12, Jan. 1993.
"The Evaluation of the Antiknocking Property of Gaseous Fuels By Means of the Methane Number and its Practical Application to Gas Engines", Dr. M. Leiker et al., pp. 1–27, (No date).

"Engine Knock Rating of Natural Gases—Methane Number", T. Callahan et al., The American Society of Mechanical Engineers, 93–ICE–18, pp. 1–12, Jan. 1993.

*Primary Examiner*—Hal Wachsman
*Attorney, Agent, or Firm*—Andrus, Sceales, Starke & Sawall

[57] ABSTRACT

A method for calculating knock resistance ratings for various blends of non-commercial grade natural gas involves the use of a computer model derived from collecting experimental data for constituent concentration levels typical in field grade natural gas. The computer model is derived using a MN (methane number) calibration curve for various natural gas compositions typical at the wellhead. The empirically-derived computer model considers concentrations of the following molar constituents: methane (60%–100%); ethane (0%–20%); propane (0%–40%); normal butane (0%–10%); normal pentane (0%–3%); mixtures of higher order hydrocarbons (0%–2%); nitrogen (0%–15%) and carbon dioxide (0%–10%). The knock characteristics of isomers of butane and pentane are accounted for by assigning fractions of their concentrations to concentrations of modeled constituents. If the concentration levels lie outside of acceptable ranges and normalization is insufficient to correct for concentration levels, an alternative method (preferably the carbon-hydrogen ratio method) is used to calculate knock resistance rating. Excessive concentrations of inert gases such as carbon dioxide and nitrogen are accounted for separately using an empirically-based algorithm, thus the model can be extended to landfill and digester gases which typically have high concentrations of carbon dioxide.

23 Claims, 6 Drawing Sheets

| TERM IN MODEL | TERM | B COEFFICIENT | X VAR.VALUE | B*X |
|---|---|---|---|---|
| CONSTANT | 0 | 45.182007 | 1 | 45.18201 |
| METHANE | 1 | 10.792912 | 0.75 | 8.094684 |
| ETHANE | 2 | -3.106283 | 0 | 0 |
| PROPANE | 3 | -48.19366 | 0.15 | -7.22905 |
| BUTANE | 4 | -108.5043 | 0.02 | -2.17009 |
| PENTANE | 5 | -285.5008 | 0.02 | -5.71001 |
| $CO_2$ | 6 | 91.941439 | 0.03 | 2.758243 |
| $N_2$ | 7 | 49.626093 | 0.03 | 1.488783 |
| HEXHEP | 8 | -363.2709 | 0 | 0 |
| METHANE*ETHANE | 9 | -91.43588 | 0 | 0 |
| METHANE*PROPANE | 10 | -149.809 | 0.1125 | -16.8535 |
| METHANE*BUTANE | 11 | -242.83333 | 0.015 | -3.6425 |
| METHANE*PENTANE | 12 | -179.6389 | 0.015 | -2.69458 |
| METHANE*$CO_2$ | 13 | 81.050253 | 0.0225 | 1.823631 |
| METHANE*$N_2$ | 14 | 86.79946 | 0.0225 | 1.952988 |
| METHANE*HEXHEP | 15 | -605.5454 | 0 | 0 |
| ETHANE*PROPANE | 16 | 210.776 | 0 | 0 |
| ETHANE*BUTANE | 17 | 497.68304 | 0 | 0 |
| ETHANE*PENTANE | 18 | 659.27811 | 0 | 0 |
| ETHANE*$CO_2$ | 19 | 10.811026 | 0 | 0 |
| ETHANE*$N_2$ | 20 | -101.7845 | 0 | 0 |
| ETHANE*HEXHEP | 21 | 1916.583 | 0 | 0 |
| PROPANE*BUTANE | 22 | 1104.1997 | 0.003 | 3.312599 |
| PROPANE*PENTANE | 23 | 1033.2556 | 0.0003 | 3.099767 |
| PROPANE*$CO_2$ | 24 | 89.998248 | 0.0045 | 0.404992 |
| PROPANE*$N_2$ | 25 | -103.9555 | 0.0045 | -0.4678 |
| PROPANE*HEXHEP | 26 | 2963.6375 | 0 | 0 |
| BUTANE*PENTANE | 27 | 3183.1816 | 0.0004 | 1.273273 |
| BUTANE*$CO_2$ | 28 | -724.0821 | 0.0006 | -0.43445 |
| BUTANE*$N_2$ | 29 | -530.8688 | 0.0006 | -0.31852 |
| BUTANE*HEXHEP | 30 | 2152.6785 | 0 | 0 |
| PENTANE*$CO_2$ | 31 | -2614.82 | 0.0006 | -1.56889 |
| PENTANE*$N_2$ | 32 | -1624.124 | 0.0006 | 0.97447 |
| PENTANE*HEXHEP | 33 | -1925.58 | 0 | 0 |
| $CO_2$*$N_2$ | 34 | -66.17702 | 0.0009 | -0.05956 |
| $CO_2$*HEXHEP | 35 | -2061.29 | 0 | 0 |
| $N_2$*HEXHEP | 36 | -1251.873 | 0 | 0 |
| METHANE$^2$ | 37 | 44.375558 | 0.5626 | 24.96125 |
| ETHANE$^2$ | 38 | 105.34981 | 0 | 0 |
| PROPANE$^2$ | 39 | 195.12588 | 0.0225 | 4.390332 |
| BUTANE$^2$ | 40 | 467.18855 | 0.0004 | 0.0186875 |
| PENTANE$^2$ | 41 | 8078.8561 | 0.0004 | 3.231542 |
| $CO_2{}^2$ | 42 | -125.8528 | 0.0009 | -0.11327 |
| $N_2{}^2$ | 43 | 43.058685 | 0.0009 | 0.038753 |
| HEXHEP$^2$ | 44 | 455.67097 | 0 | 0 |
| | | | KRR | 59.98302 |

| | | MOLE OR VOLUME % | LHV VALUE BTU/FT³ | LHV CONTRIBUTION BTU/FT³ |
|---|---|---|---|---|
| HYDROCARBONS: | | | | |
| CH4 | METHANE | 95.00 | 910 | 864.50 |
| C2H6 | ETHANE | 3.00 | 1618 | 48.54 |
| C3H8 | PROPANE | 2.00 | 2316 | 46.32 |
| I-C4H10 | ISO-BUTANE | 0.00 | 3005 | 0.00 |
| N-C4H10 | NORMAL BUTANE | 0.00 | 3013 | 0.00 |
| I-C5H12 | ISO-PENTANE | 0.00 | 3698 | 0.00 |
| N-C5H12 | NORMAL PENTANE | 0.00 | 3708 | 0.00 |
| C6H14 | HEXANE | 0.00 | 4404 | 0.00 |
| C7H16 | HEPTANE | 0.00 | 5100 | 0.00 |
| C2H4 | ETHENE | 0.00 | 1506 | 0.00 |
| C3H6 | PROPENE | 0.00 | 2186 | 0.00 |
| SUM HYDROCARBONS | | 100.00 | | 959.36 |
| NON-HYDROCARBONS: | | | | |
| N2 | NITROGEN | 0.00 | 0 | 0.00 |
| O2 | OXYGEN | 0.00 | 0 | 0.00 |
| He | HELIUM | 0.00 | 0 | 0.00 |
| CO2 | CARBON DIOXIDE | 0.00 | 0 | 0.00 |
| CO | CARBON MONOXIDE | 0.00 | 321 | 0.00 |
| H2 | HYDROGEN | 0.00 | 274 | 0.00 |
| H2S | HYDROGEN SULFIDE | 0.00 | 588 | 0.00 |
| H2O | WATER VAPOR | 0.00 | 0 | 0.00 |
| TOTAL FUEL | | 100.00 | | 959.36 |

LHV: 959.63 BTU/FT³
LHV: 35.74 MJ/NM³
SLHV: 942.67 BTU/FT³
SLHV: 35.12 MJ/NM³
KRR: 89.3

METHOD OF DETERMINING KNOCK RESISTANCE RATING FOR NON-COMMERCIAL GRADE NATURAL GAS

FIELD OF THE INVENTION

The invention accurately predicts knock characteristics of non-commercial grade natural gas in large stationary internal combustion engines. In particular, various blends of natural gas have been tested for knock characteristics, and a computer model based on the test results has been developed to calculate knock resistance ratings for various blends of non-commercial grade natural gas.

BACKGROUND OF THE INVENTION

Large natural gas engines encounter a broad range of fuels. Most of these engines do not operate on commercial grade pipeline gas. Most operate on field grade natural gas obtained directly from the wellhead, or on landfill or digester gas. These fuels have widely varying compositions and, therefore, significantly different knock tendencies.

Engine knock (i.e. fuel self-ignition) can cause premature engine damage and is thus undesirable. Knock most often occurs when engines are operated at or near rated power using low-grade fuels, although other factors can also lead to knock. If necessary, spark ignition timing can be retarded to provide acceptable knock margins when using low-grade fuels, but retarded ignition timing also derates maximum engine power output. Therefore, accurate determination of knock characteristics are important for optimizing ignition timing/power derating for engines operating on low-grade natural gas.

In the past, there have been other methods of analyzing the knock characteristics of gaseous fuels. One procedure uses a mixture of hydrogen and methane as reference fuel blends in test engines to test knock resistance for gaseous fuels. This prior method is the Methane Number (MN) test. However, prior methods have not been applied to non-commercial grade natural gas fuels. Therefore, the prior methods are inaccurate and unreliable when applied to field grade natural gas. The primary constituent field grade natural gas is methane (e.g. usually greater than 60% by volume). Other constituents include other hydrocarbon combustibles such as ethane, propane, n-butane, iso-butane, n-pentane, iso-pentane, hexane, heptane, ethene, propene; non-hydrocarbon combustibles such as hydrogen, carbon monoxide, hydrogen sulfide; inert gases such as carbon dioxide, nitrogen, helium, water vapor; and oxygen. Each of these constituents can have a substantial effect on knock resistance even in small concentrations. Prior methods do not account for the typical range of concentrations of constituents in field grade natural gas, and even ignore some typical constituents altogether.

The present methods are also largely inaccurate for predicting knock tendencies in engines operating on landfill gas or digester gas. The composition of most landfill and digester gases is a mixture of methane and carbon dioxide, but the relative concentrations of methane and carbon dioxide can vary substantially. Carbon dioxide significantly resists knock due to its ability to absorb heat. Prior models do not accurately account for the effects of widely varying concentrations of carbon dioxide which are prevalent in landfill and digester gases.

SUMMARY OF THE INVENTION

The invention is a system that quickly and accurately provides knock resistance ratings for various blends of non-commercial grade natural gas, including typical field grade natural gas, landfill gas and digester gas. The invention involves the use of an empirical model that is customized to accurately model knock characteristics in samples of natural gas for compositions characteristic of field grade natural gas (e.g. natural gas directly from the wellhead). The invention also accurately accounts for knock resistance enhancement from carbon dioxide, and thus can be reliably extended to applications involving landfill/digester gas. The invention can be easily implemented on a programmed personal computer to provide a user-friendly system of providing a knock resistance rating.

The empirical model is preferably embodied in one or more equations developed from regression analysis of experimental data obtained by testing the knock tendencies of various natural gas compositions typical of field grade natural gas. Cost savings in collecting the experimental data is facilitated by collecting experimental data only for concentration levels typical in field grade natural gas. The preferred empirically derived algorithm considers concentrations of the following molar constituents: methane (60%–100%); ethane (0%–20%); propane (0%–40%); normal-butane (0%–10%); normal-pentane (0%–3%); mixture of hexane and heptane (0%–2%); nitrogen (0%–15%); and carbon dioxide (0%–10%). For samples having gas constituent concentrations lying within expected limits, the invention is implemented in the following manner. First, concentrations of non-hydrocarbon combustibles such as hydrogen, carbon monoxide, hydrogen sulfide, etc., are temporarily removed from the analysis, and the concentration values of the above listed modeled constituents (i.e. gaseous hydrocarbon combustibles, carbon dioxide and nitrogen) are normalized. It has been found that isomers of butane (iso-butane) and pentane (iso-pentane) affect knock resistance differently than normal-pentane and normal-butane. Therefore, it is desirable to account for these isomer constituents by: 1) assigning approximately 58% of the iso-butane concentration to the propane concentration and approximately 42% of the iso-butane concentration to the n-butane concentration; and 2) assigning approximately 68% of the iso-pentane concentration to the n-butane concentration and approximately 32% of the iso-pentane concentration to the n-pentane concentration. The adjusted and normalized concentration values for the modeled constituents of the sample (e.g. the gaseous hydrocarbon combustibles, carbon dioxide, and nitrogen) are processed through the empirical model to determine a preliminary knock resistance rating. The preliminary knock resistance rating is then adjusted for non-hydrocarbon combustibles, such as hydrogen, in a manner consistent with the conventional methane number (MN) test. The resulting knock resistance rating is reliable for use in predicting knock tendencies of field grade natural gas in large stationary internal combustion engines. As mentioned above, accurate knock resistance ratings are important for optimizing ignition timing and/or engine power output for particular engines without risking the damaging effects of knock.

If the concentration of methane in the sample is less than the minimum acceptable value for the empirical model, the concentrations of inert gases such as carbon dioxide and nitrogen are removed temporarily from the modeled constituents and the remaining modeled constituents (e.g. hydrocarbon combustibles) are again normalized. The empirical model then processes in the normal manner to determine the preliminary knock resistance rating. Thereafter, the preliminary knock resistance rating is adjusted separately for both the inert gases, and for non-hydrogen combustibles. The adjustment for inert gases such as $CO_2$ is preferably based on an empirically determined algorithm (see FIG. 7).

If the concentration of any of the non-methane constituents in the empirical model exceeds the maximum acceptable level for the empirical model, an alternative model (instead of the primary empirical model) is used to calculate the knock resistance rating. The preferred alternative model is the carbon-hydrogen ratio model. As discussed with respect to the primary empirical model, the calculated knock resistance rating from the carbon-hydrogen ratio model is adjusted separately for both the inert gases, and for non-hydrogen combustibles to obtain the resulting knock resistance rating in these circumstances.

Other features and advantages of the invention may be apparent to those skilled in the art upon inspecting the following drawings and description thereof.

BRIEF DESCRIPTION OF THE DRAWINGS

FIG. 4 is a table illustrating the preferred empirical model for determining knock resistance rating for field grade natural gas in accordance with the invention.

FIG. 6 is a an example of a screen display for a computer programmed to operate in accordance with the invention.

DETAILED DESCRIPTION OF THE INVENTION

Figure 1:
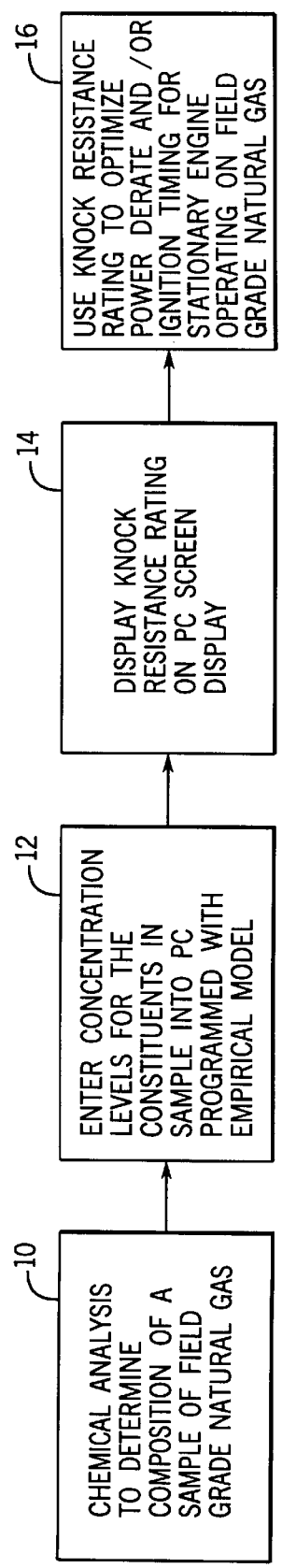
FIG. 1 is a block diagram illustrating steps taken to adjust engine operation to accommodate natural gas fuels having a low knock resistance rating for a sample of non-commercial grade natural gas.

FIG. 1 is a block diagram illustrating steps taken to determine a knock resistance rating for a sample of non-commercial grade natural gas, and then using the knock resistance rating to adjust ignition system timing and derate engine power output to accommodate gas fuels having high knock tendencies. Referring to FIG. 1, block 10 indicates that a chemical analysis (e.g., gas chromography) of a sample of the natural gas is obtained to determine the concentration levels of the various constituents in the natural gas. Concentration levels are preferably measured in terms of percentage volume for purposes of the invention, however, other ways of characterizing concentrations levels may be acceptable. Suitable analysis for purposes of the invention can be obtained from laboratories capable of analyzing methods for the analysis of inorganic and organic compounds as defined by EPA methods 8240, 8260 and 9020. The concentration levels for the constituents in the sample are entered into a personal computer, block 12. The personal computer is programmed with an empirical model 18 (FIG. 4) that accurately models knock characteristics of natural gas having constituent concentration levels characteristic of natural gas at the wellhead. The empirical model is preferably embodied in one or more mathematical algorithms derived using a non-linear, multi-variable regression analysis of experimental data as described below with respect to FIG. 4. The computer also preferably includes methods for calculating knock resistance rating when the concentration levels of the sample are beyond the levels modeled by the empirical model. Block 14 indicates that the knock resistance rating calculated by the empirical model (or the alternative method) is displayed on the screen of the personal computer. Block 16 illustrates that a person in charge of operating a stationary internal combustion engine on non-commercial grade natural gas, for instance to pump natural gas from a wellhead, uses the knock resistance rating to optimize engine power output derate and/or ignition timing. In cases where the knock resistance rating is relatively high for a particular model of engine, the stationary internal combustion engine should be able to operate at full rated power and with preferred ignition timing. On the other hand, if the knock resistance rating is relatively low for the particular engine, then it is desirable to retard ignition timing and derate the engine power output to provide an acceptable knock margin and prevent the likelihood of knock.

In the prior art, there are several methods of determining knock resistance for samples of gaseous fuel, for instance the butane number scale (BN), the methane number method (MN), and extrapolations of the motor octane number method (MON). Of these previous methods, the empirical model used in accordance with the invention is most closely related to the methane number (MN) method. However, previous MN methods concentrated on commercial grade pipeline gases, and cannot accurately be extrapolated to field grade natural gas or even landfill/digester gas. Previous MN methods were based on mixes of methane, ethane, propane and normal-butane. Field grade natural gas includes appreciable concentrations of iso-butane, n-pentane, iso-pentane, hexane, heptane, ethene and propene, which all can have significant affects on knock resistance. Also, landfill and digester gases can include large concentrations of carbon dioxide or other inert gases which also has a substantial effect on knock resistance. The invention accounts for these differences.

The empirical model referred to in block 12 of FIG. 1 is designed to accurately model knock characteristics of samples of natural gas taken from the wellhead (e.g. field grade natural gas). In order to accurately model knock characteristics for field grade natural gas, the empirical model 18 must be able to accurately predict knock characteristics for natural gas having constituent concentration levels (volume percentage) for the ranges listed in FIG. 2. There are eight listed constituents in FIG. 2 which are modeled by the empirically based algorithm in FIG. 4. These constituents are methane, ethane, protane, n-butane, n-pentane, hexane+, nitrogen, and carbon dioxide. The hexane+ designation refers to the combined concentrations of hexane, heptane, ethene, propene and possibly other higher order hydrocarbon combustibles. In specific terms, to accurately model knock tendencies of the various blends of field grade natural gases, it has been determined that the empirical model must be designed to accurately predict knock tendencies when the concentration of methane is in the range of 60%–100% (volume), the concentration of ethane is in the range of 0%–20% (volume), the concentration of propane is in the range of 0%–40% (volume), the concentration of n-butane is in the range of 0%–10% (volume), the concentration of n-pentane is in the range of 0%–3% (volume), the combined concentration of hexane, heptane, ethene, propene and other higher order hydrogen combustibles is in the range of 0%–2% (volume), the concentration of nitrogen is in the range of 0%–15% (volume), and the concentration of carbon dioxide is in the range of 0%–10% (volume). Concentrations of oxygen, helium and water vapor are added to the nitrogen concentration for purposes of FIG. 2.

Figures 2, 3:
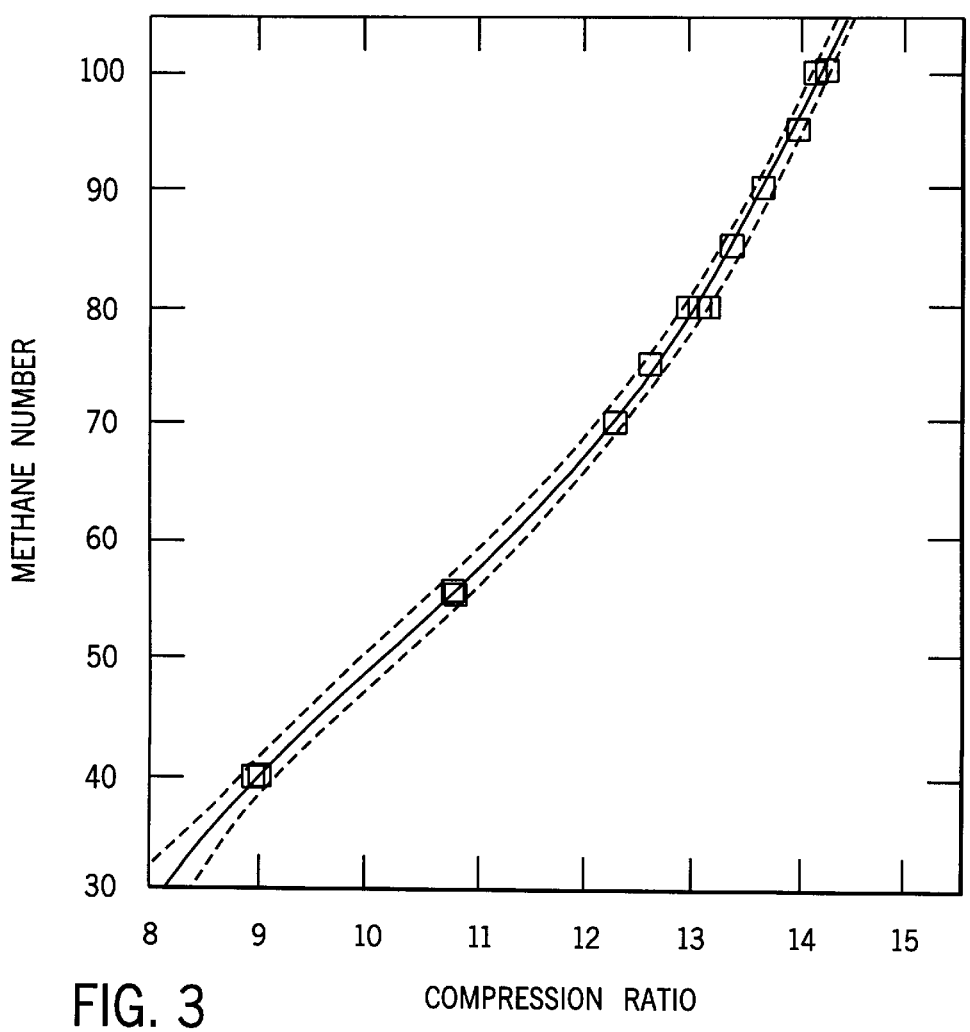
FIG. 2 is a table showing the selected concentration ranges of gas constituents characteristic of field grade natural gas that are empirically modeled in accordance with the invention.
FIG. 3 is a graph showing a methane number (MN) calibration curve.

To develop the empirical algorithm 18 in FIG. 4, various mixtures of natural gas having constituents within the ranges shown in FIG. 2 were tested in a single cylinder, variable compression ratio engine to rate knock tendency. In particular, the knock tendency of various test fuel blends were compared to the knock tendency of reference blends of methane and hydrogen. FIG. 3 shows a calibration curve for methane number (MN). MN equal to 100 represents fuel mixture of 100% methane, whereas MN equal to 0 represents a mixture of 100% hydrogen. To develop FIG. 3, a knock meter was used to determine the knock level for various methane-hydrogen blends while changing the engine compression ratio. The variable compression ratio test engine was capable of changing the compression ratio from 8:1 to 16.5:1 by raising or lowering the cylinder head assembly. A stoichiometric amount of air was supplied to the cylinder. The knock meter was adjusted to give a reading of 50% full scale on methane at a compression ratio of 14.4:1. For the other methane-hydrogen blends, the compression ratio in the cylinder was increased to achieve a 50% knock reading. The MN of the reference fuel blends was plotted against the 50% knock compression ratio to obtain the calibration curve in FIG. 3. Note that the calibration curve extends downward to an MN value of 40. Rating of the blends of test gas consisted of operating the engine on the test blend and increasing the compression ratio until the engine reached the 50% knock compression ratio used in determining the calibration curve. The MN of the test blend was then computed using the relationship between the compression ratio and the MN value as defined by the calibration curve in FIG. 3. This testing was accomplished for various mixtures of natural gas having concentrations in the ranges shown in FIG. 2. During the test, mixtures of 50% volume hexane and 50% volume heptane were used for modeling the 0%–2% hexane+ constituent. A non-linear, multi-variable regression analysis was used to fit the data and develop the algorithm 18 shown in FIG. 4.

FIG. 4 shows the preferred coefficients, column 3, for the empirical model 18, and also shows the application of the model 18 for an example sample, column 4. In the empirical model 18, each of the terms 0–44 in the algorithm are listed across a row. Term 0 is a constant value, preferably 45.182. Terms 1–8 are the empirically modeled constituents, namely concentrations of methane, ethane, propane, n-butane, n-pentane, carbon dioxide, nitrogen and a 50% mixture of hexane and heptane which is used to produce the combined concentrations of a heptane+. Terms 9–36 are cross-terms in which the empirical model 18 uses the product of the concentration of each of the respective modeled constituents. Terms 37–44 are squared terms for each of the eight modeled constituents. Column 3 shows the empirically based coefficients for the various model terms 0–44. As mentioned above, the coefficients in column 3 were determined using a non-linear, multi-variable regression analysis to fit the experimental data. The values in column 4 corresponding to terms 1–8 of the eight modeled constituents are concentration values in terms of volume for a sample of natural gas. These values correspond to data entered into the computer by a person using the invention to determine a knock resistance rating for the sample. The values in column 4 corresponding to terms 9–44 in the empirical model are calculated in the model based on the values in column 4 corresponding to entered terms 1–8. The values in column 5 of the empirical model 18 are the product of the coefficient value in column 3 and the variable values in column 4 for each respective term. The values in column 5 of model 18 are summed to obtain the pulmonary knock resistance rating (KRR) for the sample, reference numeral 20. Note that in general, certain constituents such as methane, carbon dioxide and nitrogen generally enhance knock resistance and thus increase the knock resistance ratio 20.

Figure 5:
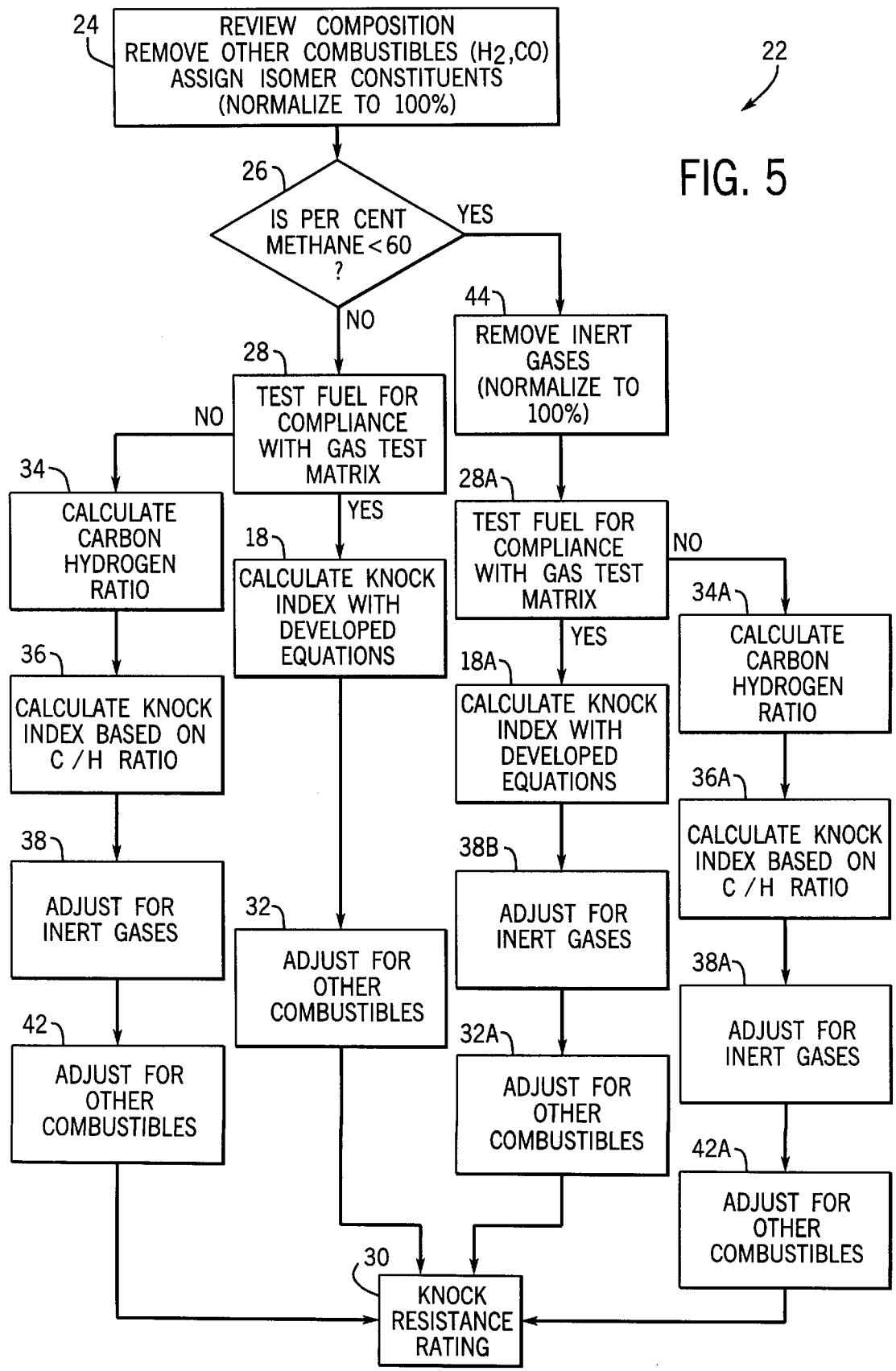
FIG. 5 is a block diagram illustrating the preferred method of determining knock resistance rating for a sample of field grade natural gas in accordance with the invention.

While the empirical model 18 in FIG. 4 accounts for concentration levels of hydrocarbon combustibles, carbon dioxide and nitrogen falling within the ranges shown in FIG. 2, field grade natural gas, as well as landfill and digester gas, may have constituent concentrations outside of these ranges, or may include other constituents that affect knock tendency. For instance, there may be significant concentrations of non-hydrocarbon combustibles, or inert gases that effect knock characteristics. FIG. 5 illustrates the preferred computer scheme 22 for accounting for these types of discrepancies. The computer scheme 22 shown in FIG. 5 includes the empirical model 18, but also contains steps to account for situations in which the constituent concentrations fall outside of the ranges shown in FIG. 2.

In FIG. 5, block 24 indicates that the concentration values of the various molar constituents of the sample of natural gas are reviewed. The concentration values are separated into a group of modeled constituents and into a group of non-hydrocarbon combustible constituents. The group of modeled constituents is the group of 8 modeled constituents shown in FIGS. 2 and 4, i.e. terms 1–8 in FIG. 4 (methane, ethane, propane, butane, pentane, carbon dioxide, nitrogen, and hexane/heptane). The group of non-hydrogen combustible constituents includes concentration values for hydrogen, carbon monoxide, hydrogen sulfide or similar constituents present in the sample. Block 24 also indicates that the scheme 22 accounts for concentration levels of isomers for the modeled constituents which significantly affect knock resistance rating, namely iso-butane and iso-pentane. Preferably, concentrations of iso-butane are accounted for by assigning approximately 58% of the concentration value of iso-butane to the concentration value of propane and assigning approximately 42% of the concentration level of iso-butane to the concentration of normal-butane. In a similar fashion, concentration levels of iso-pentane are accounted for by assigning approximately 68% of the concentration value of iso-pentane to the concentration value of n-butane and assigning approximately 30% of the concentration value of iso-pentane to the concentration value of n-pentane. As long as isomer constituents are accounted for, for instance as described above, it is not necessary that these isomer constituents be modeled directly by the empirical model 18.

Block 24 finally indicates that the concentration values for the modeled constituents (i.e. terms 1–8 in FIG. 4) are normalized to 100%. In order to assure that the normalized concentration levels of the modeled constituents are acceptable for the empirical model 18, the concentration levels for the modeled constituents are compared to limit values before inputting the normalized concentration values into the empirical model. In particular, block 26 illustrates that the normalized concentration value for methane is first compared to a minimum concentration limit value. The minimum concentration limit value for methane is preferably about 60% volume, which corresponds to the methane concentration range of FIG. 2. If the concentration level of methane is greater than the minimum limit value of 60% volume, block 26 illustrates that the normalized concentration values of the non-methane molar constituents in the group of model constituents (i.e. ethane, propane, n-butane, n-pentane, hexane+, nitrogen, carbon dioxide) are compared to maximum concentration limit values defined for each of the respective non-methane modeled constituents. Assuming that the normalized concentration values for the non-methane molar constituents in the group of modeled constituents is also within acceptable limits (see FIG. 2), the empirical model 18 is used to calculate a preliminary knock resistance rating. Block 32 illustrates that the preliminary knock resistance rating calculated by the empirical model 18 is then adjusted to account for the concentration levels of the non-hydrocarbon combustibles which were earlier removed from the analysis, see block 24. To adjust for the concentration levels of the non-hydrocarbon combustibles, the concentration values of hydrogen, carbon monoxide and hydrogen sulfide are combined, and the preliminary knock resistance rating from the empirical model 18, is adjusted by subtracting the combined concentration value (i.e. combined volume percent) of hydrogen, hydrogen sulfide and carbon monoxide from the preliminary knock resistance rating determined from the empirical model 18. Block 30 in FIG. 5 represents that the adjustment for non-hydrocarbon combustibles results in the final knock resistance rating.

Figure 7:
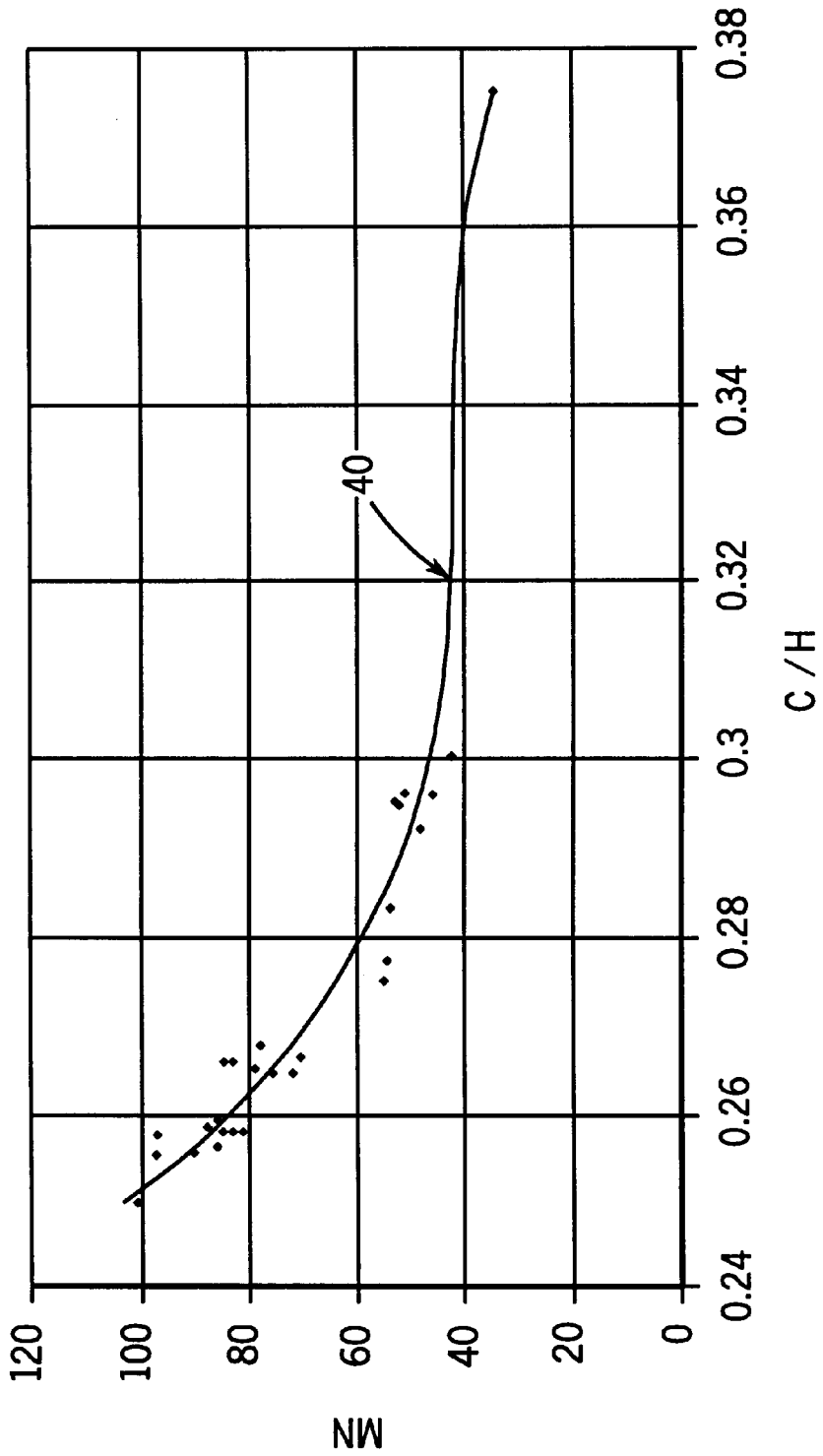
FIG. 7 is a graph illustrating the correspondence between the carbon-hydrogen ratio method of determining knock resistance rating and the methane number method of determining knock resistance rating.

Referring again to block 28 in FIG. 5, if one or more of the normalized concentration values for any one of the non-methane molar constituents in the group of modeled constituents exceeds the respective maximum concentration limit, an alternative model 34, 36, 38, 42, instead of the primary empirical model 18, is used to determine the knock resistance rating for the sample. The preferred alternative model is the carbon-hydrogen ratio model. Block 34 indicates that the overall carbon-hydrogen ratio be calculated for the hydrocarbon combustible constituents (i.e., multiply concentration level by carbon-hydrogen ratio of respective constituents, and sum results). A preliminary knock resistance rating is then determined based on the carbon-hydrogen ratio, block 36. Preferably, the carbon-hydrogen ratio model is embodied in a third order linear equation relating the carbon-hydrogen ratio to methane number MN. The preferred third order algorithm is shown on FIG. 7 by reference number 40. Algorithm 40 is determined from a least squares fit of experimental data relating the carbon-hydrogen ratio to MN number. Other alternative methods besides the carbon-hydrogen ratio method are possible within the scope of the invention. For instance, the hydrogen-carbon ratio method, fuel molecular weight method, or heating value method may be suitable. Testing has shown that the carbon-hydrogen ratio method (FIG. 7) is the most accurate of the alternative methods tested.

The carbon-hydrogen ratio method does not account for concentrations of inert gases such as carbon dioxide, nitrogen or helium. Thus, the preliminary knock resistance rating determined from the carbon-hydrogen ratio method is adjusted for concentrations of these inert gases, block 38. Specifically, it has been found through testing that concentrations of carbon dioxide improve knock resistance due to heat absorption. The amount of improvement due to carbon dioxide concentrations can be approximated by the following equation:

$$KRR \text{ improvement} = 0.304 \text{ (volume \% } CO_2) + 0.008 \text{ (volume \% } CO_2)^2 \quad \text{(Eq. 1)}$$

It has also been found that other inerts such as nitrogen, helium or water vapor improve knock resistance slightly, but not to the extent as carbon dioxide. Concentrations of oxygen also slightly improve knock resistance rating. In the preferred embodiment of the invention, the concentrations of nitrogen, oxygen, helium and water vapor are combined, and approximately $\frac{1}{13}$ of the combined concentration is added to the concentration of $CO_2$ before applying Equation 1.

Block 42 indicates that after adjusting the knock resistance rating for inert gases, the knock resistance rating is then adjusted for non-hydrogen combustibles. The adjustment at block 42 is done in the same manner as explained above with respect to block 32.

Referring again to block 26 in FIG. 5, if the concentration level of methane falls below the minimum concentration limit value, e.g. falls below 60% volume, the concentrations values for inert gases such as carbon dioxide and nitrogen, are temporarily removed from the analysis and the concentration values of the combustible components in the group of model constituents (e.g. methane, ethane, propane, butane, and pentane) are again normalized to 100%, block 44. Block 28A illustrates that the twice normalized concentration levels for the modeled combustible constituents are tested for compliance within acceptable limits for the empirical model 18. If one or more of the twice normalized concentration levels lies outside of the acceptable limits, the knock resistance rating is determined in accordance with the alternative carbon hydrogen ratio method, 34a, 36a, 38a and 42a which is accomplished generally in the same manner as discussed previously with respect to blocks 34, 36, 38 and 42. If the twice normalized concentration levels lie within the acceptable limit values, a preliminary knock resistance rating is calculated using the empirical model 18A, which is preferably the same as indicated by block 18 (i.e., preferably the same computer model 18 as in FIG. 4). The preliminary knock resistance rating is then adjusted concentration values for inert gases that were temporarily removed from the analysis, block 38b, preferably in the same manner as discussed previously with respect to block 38 and Equation 1. The knock resistance rating is then adjusted for non-hydrocarbon combustibles, block 32a, as discussed above with respect to block 32.

FIG. 6 shows a screen display for a personal computer programmed to determine knock resistance rating (KRR) in accordance with the invention. The screen display 48 includes a tabulation of typical hydrocarbon and non-hydrocarbon constituents for non-commercial grade natural gas; namely: methane, ethane, propane, iso-butane, normal butane, iso-pentane, normal pentane, hexane, heptane, ethene, propene, nitrogen, oxygen, helium, carbon dioxide, carbon monoxide, hydrogen, hydrogen sulfide and water vapor. The screen display includes a column 50 labeled mole or volume percent. A user of the computer program is prompted to input concentration data in column 50 for the respective constituent. Based on the inputs in column 50, the programmed computer runs the scheme 22 shown in FIG. 5, and calculates a knock resistance rating (KRR) which is displayed in the upper right-hand corner of the screen display 48 as indicated by reference numeral 52. It is also preferred that the display 48 show calculations relating to the lower heating value of the fuel. Column 54 lists lower heating values for the various constituents listed on the screen display 48, and column 56 is calculated by the computer to list lower heating value contribution for each of the various constituents of the sample. The knock resistance rating (KRR) and the lower heating value information can then be used to optimize engine operation for the particular full composition.

It is recognized that various alternatives, modifications and equivalents may be apparent to those skilled in the art. The following claims should be interpreted to cover such alternatives, modifications and equivalents.

I claim:

1. A method of providing a knock resistance rating valve for a sample of gaseous fuel, the method comprising the steps of:
   a) determining concentration values of the various molar constituents of the sample of gaseous fuel;
   b) separating the concentration values of the various molar constituents into concentration values for a group of non-hydrocarbon combustible constituents and concentration values for hydrocarbon combustible components in a group of modeled constituents which includes concentrations of methane, ethane, propane, n-butane, n-pentane, nitrogen, and carbon dioxide and the combined concentration of hexane, heptane and any other higher order hydrocarbon combustibles that may be present and which accounts for concentrations of isomers of the modeled constituents;
   c) normalizing the concentration values of the constituents in the group of modeled constituents;
   d) using an empirical model to determine a knock resistance rating value for the sample of gaseous fuel from the normalized concentration values of the constituents in the group of modeled constituents, the empirical model being customized to accurately account for the effects of the modeled constituents and of isomers of the modeled constituents on a knock resistance rating value to model knock characteristics of the sample of gaseous fuel;
   e) adjusting the knock resistance rating value to account for the concentration level of molar constituents in the group of non-hydrocarbon combustible constituents; and
   f) displaying the knock resistance rating value.

2. A method as recited in claim 1 wherein the sampled gaseous fuel is selected from the group consisting of natural gas, digester gas, wellhead gas and landfill gas.

3. A method as recited in claim 1 further comprising the steps of:
   before using the empirical model to determine the knock resistance rating value for the gaseous fuel sample, comparing each of the normalized concentration values of the non-methane molar constituents in the group of modeled constituents to maximum concentration limit values defined for each of the non-methane modeled constituents; and
   if the normalized concentration value for any one of the non-methane molar constituents in the group of modeled constituents exceeds the respective maximum concentration limit value, using an alternative knock resistance rating model instead of the empirical model to determine the knock resistance rating value for the gaseous fuel sample.

4. A method as recited in claim 3 wherein the alternative knock resistance rating model is a carbon-hydrogen ratio model.

5. A method as recited in claim 3 further comprising the steps of:
   after the knock resistance rating value for the gaseous fuel sample is determined from the alternative knock resistance rating model and before displaying the knock resistance rating value, adjusting the knock resistance rating value to account for the concentration level of the molar constituents in the group of non-hydrocarbon combustible constituents.

6. A method as recited in claim 3 further comprising the step of:
   after the knock resistance rating value for the gaseous fuel sample is determined from the alternative knock resistance rating model and before displaying the knock resistance rating value, adjusting the knock resistance rating value to account for concentration levels of inert gases in the gaseous fuel sample.

7. A method as recited in claim 1 further comprising the steps of:
   before using the empirical model to determine the knock resistance rating value for the gaseous fuel sample, comparing the normalized concentration value for methane to a minimum concentration limit value for methane; and
   if the normalized concentration value for methane is less than the minimum concentration limit value for methane, separating a concentration level value of inert gases from concentration level values of hydrocarbon combustible components in the group of modeled constituents and again normalizing the concentration values of the hydrocarbon combustible components in the group of modeled constituents, and then using the empirical model to determine the knock resistance rating value for the gaseous fuel sample from the twice normalized concentration values of the hydrocarbon combustible components in the group of modeled constituents.

8. A method as recited in claim 7 further comprising the step of:
   after the knock resistance rating value for the gaseous fuel sample is determined from the empirical model and before displaying the knock resistance rating value, adjusting the knock resistance rating value to account for the concentration level value of the inert gasses.

9. A method as recited in claim 7 further comprising the step of:
   after the knock resistance rating value for the gaseous fuel sample is determined from the empirical model and before displaying the knock resistance rating value, adjusting the knock resistance rating value to account for the concentration level of molar constituents in the group of non-hydrocarbon combustible constituents.

10. A method as recited in claim 7 further comprising the steps of:
    before using the empirical model to determine the knock resistance rating value for the gaseous fuel sample, comparing each of the twice normalized concentration values of the hydrocarbon combustible components in the group of modeled constituents other than methane to maximum concentration limit values defined for each of the modeled constituents; and
    if the twice normalized concentration value for any non-inert, non-methane molar constituents in the group of modeled constituents exceeds the respective maximum concentration limit value, using an alternative knock resistance rating model instead of the empirical model to determine the knock resistance rating value for the gaseous fuel sample.

11. A method as recited in claim 10 wherein the alternative knock resistance rating model is a carbon-hydrogen ratio model.

12. A method as recited in claim 10 further comprising the step of:

after the knock resistance rating value for the gaseous fuel sample is determined from the alternative knock resistance rating model and before displaying the knock resistance rating value, adjusting the knock resistance rating value to account for concentration levels of inert gases in the gaseous fuel sample.

13. A method as recited in claim 10 further comprising the step of:

after the knock resistance rating value for the gaseous fuel sample is determined from the alternative knock resistance rating model and before displaying the knock resistance rating value, adjusting the knock resistance rating value to account for the concentration of the molar constituents in the group of non-hydrocarbon combustible constituents.

14. A method as recited in claim 7 wherein the minimum concentration percentage limit value for methane is approximately 60% volume.

15. A method as recited in claim 1 wherein the step of accounting for concentrations of isomers of the hydrocarbon combustible components in the group of modeled constituents is accomplished by assigning a first fraction of a concentration value of an isomer constituent to a concentration value of one of the hydrocarbon combustible components in the group of modeled constituents and assigning a second fraction of the concentration value of the isomer constituent to the concentration value of another of the hydrocarbon combustible components in the group of modeled constituents.

16. A method as recited in claim 15 wherein the isomer constituent is iso-butane and approximately 58% of the concentration value of iso-butane is added to the concentration value of propane and approximately 42% of the concentration value for iso-butane is added to the concentration value of n-butane.

17. A method as recited in claim 15 wherein the isomer constituent is iso-pentane and approximately 68% of the concentration value of iso-pentane is added to the concentration value of butane and approximately 32% of the volume percentage value of iso-pentane is added to the concentration value of n-pentane.

18. A method as recited in claim 15 wherein the isomer constituent is an isomer of a first molar constituent in the group of modeled constituents, and the method further comprising the step of accounting for a second isomer constituent that is an isomer of a second molar constituent in the group of modeled constituents by assigning a first fraction of the concentration value of the second isomer constituent to the concentration value of one of the non-isomer constituents in the group of modeled constituents and a second fraction of the concentration value of the second isomer constituent to another concentration value of the hydrocarbon combustible components in the group of modeled constituents.

19. A method as recited in claim 1 wherein the empirical model is embodied in one or more algorithms created by the use of a non-linear, multi-variable regression analysis of experimental data.

20. A method as recited in claim 1 wherein the empirical model models knock tendencies for a sample of a gaseous fuel having concentration of methane in the range of 60%–100% volume, concentration of ethane in the range of 0%–20% volume, concentration of propane in the range of 0%–40% volume, concentration of n-butane in the range of 0%–10% volume, concentration of n-pentane in the range of 0%–3% volume, the combined concentration of n-pentane in the range of 0%–3% volume, the combined concentration of hexane, heptane and other hydrocarbon combustibles having a higher order than heptane in the range of 0%–2% volume, concentration of nitrogen in the range of 0%–15% volume, and concentration of carbon dioxide of 0%–10% volume.

21. A system for providing a knock resistance rating value for a sample of a gaseous fuel comprising:

a programmed computer having a screen display and data input means;

means on the screen display for prompting a user to enter fuel composition data for all molar constituents of the sample of gaseous fuel into the data input means;

means for separating the fuel composition data into data for a group of modeled constituents including methane, ethane, propane, n-butane, n-pentane, a mixture of hexane, heptane, and any other higher order hydrocarbon combustibles that may be present, and nitrogen and carbon dioxide and a group of non-hydrocarbon combustible constituents and for accounting for isomers of the modeled constituents;

means for normalizing the fuel composition data for the molar constituents in the group of modeled constituents; and means for determining a knock resistance rating value from the normalized fuel composition data for the molar constituents in the group of modeled constituents, said means for determining a knock resistance rating value including an empirical model being customized to accurately model knock characteristics of samples of gaseous fuel from the normalized fuel composition data for the modeled constituents and for isomers of the modeled constituents;

means for adjusting the knock resistance rating value to account for the fuel composition data of molar constituents in the group of non-hydrocarbon combustible constituents; and means for displaying the knock resistance rating value on the screen display.

22. A system as recited in claim 21 wherein the empirical model is embodied in one or more algorithms developed from a non-linear, multi-variable regression analysis of experimental data.

23. A system as recited in claim 21 wherein the empirical model models knock tendencies for a sample of a gaseous fuel having concentration of methane in the range of 60%–100% volume, concentration of ethane in the range of 0%–20% volume, concentration of propane in the range of 0%–40% volume, concentration of n-butane in the range of 0%–10% volume, concentration n-pentane in the range of 0%–3% volume, the combined concentration of hexane, heptane and other hydrocarbon combustibles of higher order than heptane in the range of 0%–2% volume, concentration of nitrogen in the range of 0%–15% volume, and concentration of carbon dioxide of 0%–10% volume.

* * * * *